(12) United States Patent
Floyd et al.

(10) Patent No.: US 11,498,983 B2
(45) Date of Patent: Nov. 15, 2022

(54) LIGHT-ACTIVATED COATING AND MATERIALS

(71) Applicants: William Clary Floyd, Chester, SC (US); Josef S Schneider, Raleigh, NC (US); Bernard W Wolff, Roswell, GA (US)

(72) Inventors: William Clary Floyd, Chester, SC (US); Josef S Schneider, Raleigh, NC (US); Bernard W Wolff, Roswell, GA (US)

( * ) Notice: Subject to any disclaimer, the term of this patent is extended or adjusted under 35 U.S.C. 154(b) by 915 days.

(21) Appl. No.: 16/088,059

(22) PCT Filed: Mar. 24, 2017

(86) PCT No.: PCT/US2017/024162
§ 371 (c)(1),
(2) Date: Sep. 24, 2018

(87) PCT Pub. No.: WO2017/165861
PCT Pub. Date: Sep. 28, 2017

(65) Prior Publication Data
US 2020/0299438 A1  Sep. 24, 2020

Related U.S. Application Data

(60) Provisional application No. 62/313,231, filed on Mar. 25, 2016.

(51) Int. Cl.
*C08F 220/06* (2006.01)
*C08F 20/00* (2006.01)
(Continued)

(52) U.S. Cl.
CPC .............. *C08F 20/00* (2013.01); *A61K 31/78* (2013.01); *C08F 212/08* (2013.01);
(Continued)

(58) Field of Classification Search
CPC .. C08F 20/00; C08F 220/1804; C08F 212/08; C08F 220/06; A61K 31/78;
(Continued)

(56) References Cited

U.S. PATENT DOCUMENTS 4,814,514 A * 3/1989 Yokota ...................... C08F 2/26
568/675
5,431,845 A * 7/1995 Akhavan-Tafti ....... G01N 21/76
252/301.16

(Continued)

OTHER PUBLICATIONS

Pessoni et al. Langmuir 2013, 29, 10264-10271. dx.doi.org/10.1021/la402079z.*

(Continued)

*Primary Examiner* — Robert S Jones, Jr.
*Assistant Examiner* — Jiangtian Xu
(74) *Attorney, Agent, or Firm* — Howard M. Gitten, Esq.; Lewis Brisbois Bisgaard & Smith LLP

(57) ABSTRACT

A polymer having a first monomer operatively connected to Rose Bengal, a second monomer, and a surfactant, wherein the surfactant is selected from the group consisting of ionic surfactants, anionic surfactants, cationic surfactants, nonionic surfactants, zwitterionic surfactants, and mixtures thereof. The Rose Bengal in polymer in an amount effective for rendering the polymer antimicrobial or antiviral upon exposure of said polymer to light; and the polymer produces singlet oxygen from air in the presence of light. A substrate have these features is also included.

9 Claims, 1 Drawing Sheet

(51) Int. Cl.
*A61K 31/78* (2006.01)
*C08F 212/08* (2006.01)
*C08K 5/00* (2006.01)
*C09B 11/24* (2006.01)
*C09B 69/10* (2006.01)
*D06P 1/00* (2006.01)
*C08F 220/18* (2006.01)
*A61K 9/00* (2006.01)

(52) U.S. Cl.
CPC ...... *C08F 220/06* (2013.01); *C08F 220/1804* (2020.02); *C08K 5/0041* (2013.01); *C09B 11/24* (2013.01); *C09B 69/103* (2013.01); *D06P 1/0052* (2013.01); *A61K 9/0043* (2013.01)

(58) Field of Classification Search
CPC .... A61K 9/0043; C08K 5/0041; C09B 11/24; C09B 69/103; D06P 1/0052
See application file for complete search history.

(56) References Cited

U.S. PATENT DOCUMENTS

| | | | | |
|---|---|---|---|---|
| 5,830,526 | A * | 11/1998 | Wilson | D06P 1/5278 427/2.1 |
| 5,858,746 | A * | 1/1999 | Hubbell | C08B 37/003 435/177 |
| 6,545,102 | B1 * | 4/2003 | Akhavan-Tafti | C08F 8/44 525/217 |
| 9,480,760 | B2 * | 11/2016 | Appeaning | A61L 2/088 |
| 2003/0095916 | A1 * | 5/2003 | Akhavan-Tafti | C08F 8/18 423/579 |
| 2007/0238660 | A1 * | 10/2007 | Michielsen | A61P 31/12 514/183 |
| 2009/0209679 | A1 * | 8/2009 | Dreher | C08F 265/06 526/341 |
| 2012/0100039 | A1 * | 4/2012 | Appeaning | A61L 2/088 422/22 |
| 2013/0210156 | A1 * | 8/2013 | Wooley | G01N 21/75 436/63 |
| 2014/0187451 | A1 * | 7/2014 | Tamsilian | C08F 265/06 507/213 |
| 2020/0299438 | A1 * | 9/2020 | Floyd | C12Q 1/18 |

OTHER PUBLICATIONS

Pellach et al. Journal of Photochemistry and Photobiology A: Chemistry 228 (2012) 60-67.*
Nowakowska et al. Pure Appl. Chem., vol. 73, No. 3, pp. 491-495, 2001.*
Kim et al ("Photodynamic antifungal activities of nanostructured fabrics grafted with rose bengal and phloxine B against Aspergillus fumigatus", J. Appl. Polym. Sci. 2015) (Year: 2015).*
Chen, et al..: "Energy-Free, Singlet Oxygen-Based Chemodynamic Therapy for Selective Tumor Treatment without Dark Toxicity", Adv Healthc Mater . Sep. 2019;8(18):e1900366. doi: 10.1002/adhm. 201900366. Epub Jul. 31, 2019.
Qin, et al.: "Light-Controlled Ge eration of Singlet Oxygen within a Discrete Dual-Stage Metallacycle for Cancer Therapy", J Am Chem Soc. Jun. 5, 2019;141(22):8943-8950. doi: 10.1021 /jacs. 9b02726. Epub May 23, 2019.
Nowis, et al.: "The influence of photodynamic therapy on the immune response", Photodiagnosis Photodyn Ther. Dec. 2005;2(4):283-98. doi: 10.1016/S1572-1000(05)00098-0. Epub Dec. 5, 2005.
Zhou, et al.: "Activatable Singlet Oxygen Generation from Lipid Hydroperoxide Nanoparticles for Cancer Therapy", Angew Chem Int Ed Engl. Jun. 1, 2017;56(23):6492-6496. doi: 10.1002/anie. 201701181. Epub May 4, 2017.
Wang, et al.: "Lifetime and diffusion distance of singlet oxygen in air under everyday atmospheric conditions". From the journal: Physical Chemistry Chemical Physics, Issue 38, 2020.
Zhang, et al., Functional Dye as a Comonomer in a Water-Soluble Polymer; Journal of Polymer Chemistry 2015, 53, 1594-1599, DOI: 10.1002/pola.27592.

* cited by examiner

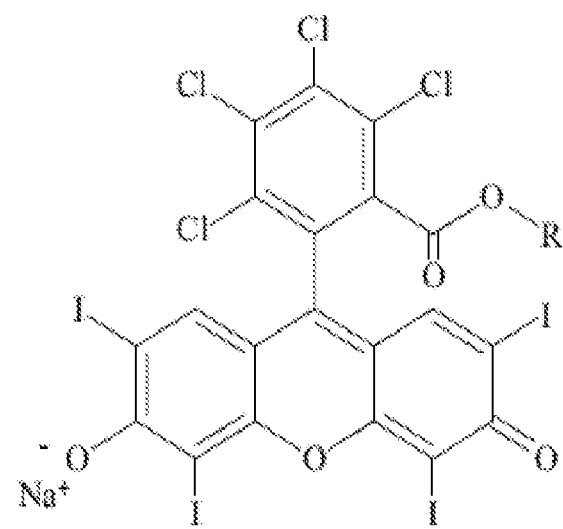

LIGHT-ACTIVATED COATING AND MATERIALS

CROSS-REFERENCE TO RELATED APPLICATION

This application claims priority to and the benefit of U.S. patent application Ser. No. 62/313,231 filed on Mar. 25, 2016, the entirety of which is incorporated herein by reference.

TECHNICAL FIELD

This disclosure relates to temporary coatings having light-activated properties, and methods for applying and removing temporary coatings. This application relates to coatings for surfaces and more particularly to anti-microbial coatings. This application also provides compositions and methods for preventing and treating infections and has applications in the areas of medicine, pharmacology, virology, and medicinal chemistry.

BACKGROUND

There are very few good options for preventing or treating infections, including "common colds." In the prior art no fast working and efficient composition has been provided for preventing and/or treating common colds initiated by viral infections caused by the cold viruses, such as rhino virus, corona virus, adenovirus, coxsackie virus, RS-virus, echovirus or other cold viruses yielding the usual well known cold syndromes in patients. Practically all humans suffer 2 to 3 times a year from infections in the upper respiratory passages, such as cold and flu. In general, the majority of common colds occurring in September, October and November are caused by rhinovirus infection, whereas the majority of common cold occurring in January, February and March are caused by Coronavirus infections. Furthermore, there is a great need for effective remedies in the increasing number of patients suffering from allergic syndromes, for example asthma, which may be initiated by common cold viruses, especially the rhinovirus.

Rose Bengal has long been known in the biological community as a staining agent for tissue. It has been used in eye drops to stain damaged corneal tissue. In synthetic organic chemistry it has been used as a photocatalyst to generate singlet oxygen, which is the electronically excited state of ordinary molecular oxygen. Singlet oxygen has a short half-life under normal conditions ranging from milliseconds to nanoseconds. Its half-life in solvents is milliseconds/nanoseconds, but has been reported in minutes in air. Singlet oxygen rapidly decays back to ordinary ground-state triplet oxygen by reacting with other molecular species and transferring its excitation energy or undergoing a chemical reaction. This singlet oxygen has also shown a sanitizing effect in eliminating harmful bacteria and viruses. Singlet oxygen generated from numerous photocatalytic sources has been shown to be a safe and effective antimicrobial technology. Delivery and associated hazardous effects have created issues with the use and delivery of singlet oxygen.

Accordingly, there is always a need for improved methods and systems for preventing the spread and treating infections. It is to those needs, among others, that this application is directed.

SUMMARY

One aspect of this application is a polymer having a first monomer operatively connected to dye (e.g., Rose Bengal), a second monomer, and a surfactant. The surfactant is selected from the group of ionic surfactants, anionic surfactants, cationic surfactants, nonionic surfactants, zwitterionic surfactants, and mixtures thereof. The Rose Bengal or the dye in polymer in an amount effective for rendering the polymer antimicrobial or antiviral upon exposure of the polymer to light; and the polymer produces singlet oxygen from air in the presence of light.

Another aspect of this application a method of treating an immune reaction in a mammal. The method includes administering locally (one or more times) to nasal passages of the mammal singlet oxygen from a coating. The coating has a polymer of a first monomer operatively connected to a dye (e.g., Rose Bengal), a second monomer, and a surfactant, wherein the surfactant is selected from the group consisting of ionic surfactants, anionic surfactants, cationic surfactants, nonionic surfactants, zwitterionic surfactants, and mixtures thereof. The Rose Bengal in the polymer is in an amount effective for rendering the polymer antimicrobial or antiviral upon exposure of said substrate to light; and the polymer produces singlet oxygen from air in the presence of light.

FIGURES

FIG. 1 represents illustrative examples of a first monomer connected to a dye (e.g., Rose Bengal).

DETAILED DESCRIPTION

Specific embodiments of this disclosure include a polymer-bound version of Rose Bengal and other dyes. The Rose Bengal molecule, e.g., may be modified to incorporate functionality, of the Rose Bengal, into a molecule or monomer that may be polymerized or co-polymerized with cationic, nonionic or anionic monomers (e.g., vinyl and acrylic monomers). In specific embodiments, the monomers may be polymerized by using free-radical polymerization. Both an aqueous solution polymer and an aqueous emulsion polymer incorporating the monomers have been developed.

Accordingly, in one aspect, the present teaching provides a process for the preparation of an antimicrobial coating solution, the process of polymerizing certain monomers and dyes to form a coating suitable for application to a surface. The coating can be placed on a substrate/surface as a thin homogeneous coating to be applied to a substrate (in this context, the term "thin" can mean approximately 10 nm to 400 nm thickness for a single layer) and still provide for effective antimicrobial action, the end product being transparent to the user.

One or more of the foregoing dyes is effective against one or more of the following bacteria: *Escherichia coli, Pseudomonas aeroginosa, Enterobacter cloacae, Staphylococcus aureus, Enterococcus faecalis, Klebsiella pneumoniae, Salmonella typhimurium, Staphylococcus epidermidis, Serratia marcescens, Mycobacterium bovis* (TB), methicillin resistant *Staphylococcus aureus* and *Proteus vulgaris*. In addition, the foregoing dyes are effective against viruses, particularly enveloped viruses, such as Herpes, HIV, and viruses associated with the "common cold."

The first monomer for use with specific embodiments is operatively linked to a dye that absorb light, become excited and transfer that excitation energy to molecular oxygen (O2), exciting it from the electronic ground state triplet to the excited singlet state. The dye acts as a light-activated catalyst for generating singlet oxygen. The singlet oxygen is highly reactive and disables virus and bacteria on contact.

One example is the alkali metal salts of Rose Bengal, 4,5,6,7-tetrachloro-2',5',7'-tetraiodo fluorescein sodium or potassium.

Several dyes have been examined and modified to allow their incorporation into polymers via free radical polymerization. FIG. 1 shows a representative example of a dye connected to a first monomer, wherein the R represents a stryenic group, an acrylic group, or another covalently bound group capable of further polymerization or copolymerization. In one example, R can be ortho, meta or para vinyl benzyl, ortho, meta or para alpha methyl vinyl benzyl, ethyl acrylate, ethyl methacrylate, ethyl crotonate, ethyl acrylamido, ethyl methacrylamido. That is, e.g.,

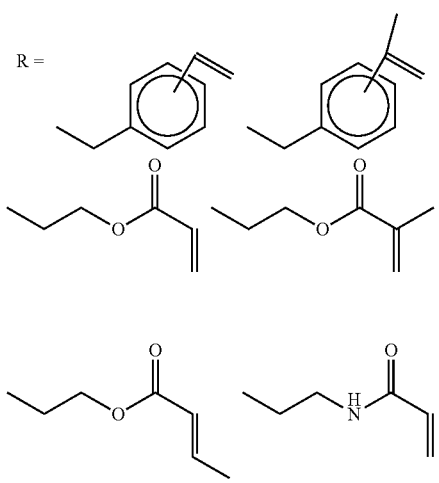

Rose Bengal has been the dye of choice for various reasons, and has been modified to contain either a styrenic or acrylic handle. In certain examples, a styrene group or an acrylic group was added to the carboxylic acid group of Rose Bengal. For example:

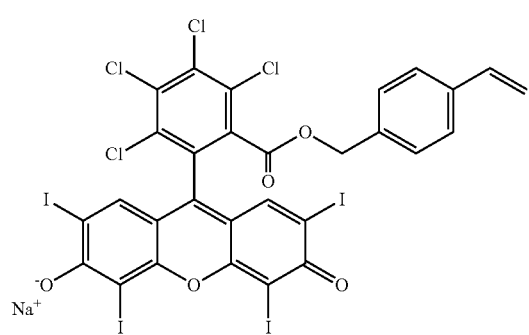

(I)

For another example:

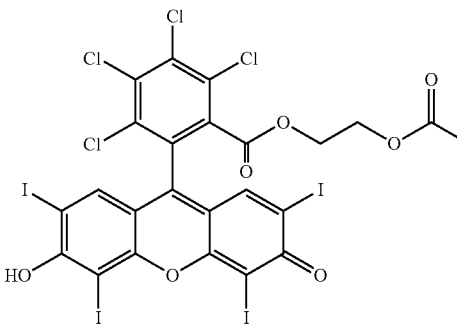

(II)

For another example,

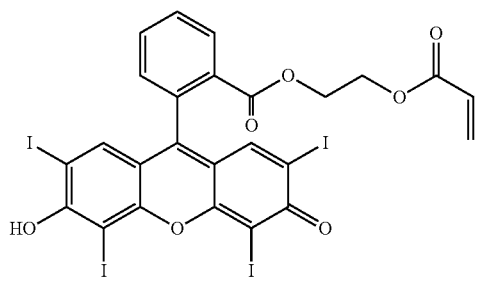

(III)

For another example,

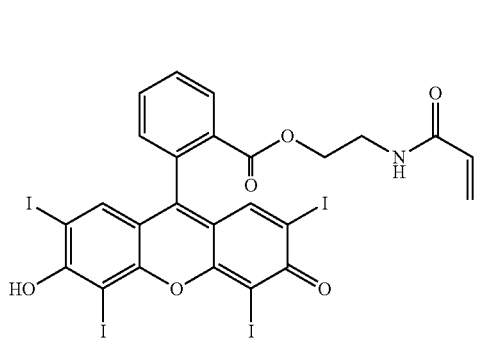

(IV)

For another example,

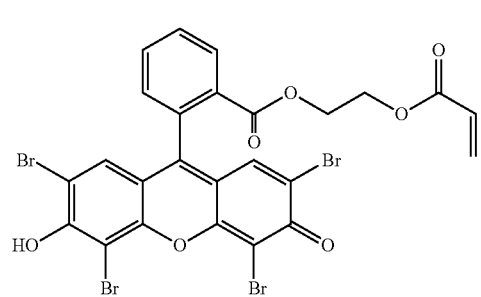

(V)

For another example,

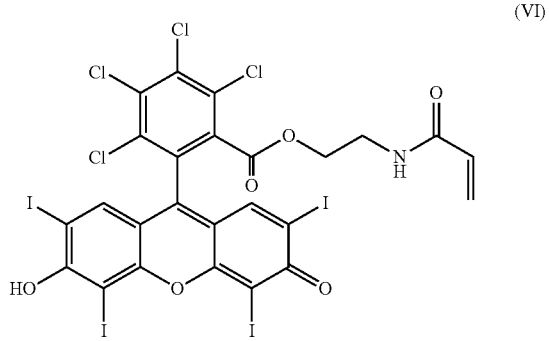 [SMILES: C=CC(=O)NCCOC(=O)c1c(Cl)c(Cl)c(Cl)c(Cl)c1-c1c2cc(I)c(=O)c(I)c-2oc2c(I)c(O)c(I)cc12]

(VI)

In certain embodiments, the polymer may contain styrenic and acrylic Rose Bengal derivatives, which have been copolymerized with various vinyl and acrylic monomers. Rose Bengal, is a synthetic dye, 2,4,5,7-tetraiodo-3', 4', 5', 6'-tetrachlorofluorescein. Rose Bengal is a typical photosensitizer to produce singlet oxygen, which can be used to kill microbes. Rose Bengal has many derivatives. The most common one is the sodium salt form, which is highly water soluble.

A solution polymer and an emulsion polymer have been developed for various applications. The solution polymer comprised various water-soluble monomers such as acrylic acid, itaconic acid and hydroxyethyl acrylate. It also can incorporate copolymerizable surfactants such as allyl alcohol/I OEO or lauryl alcohol polyoxyethylene ammonium sulfate with a pendant allyl group. These surfactants were used to lower surface tension to enable the polymer to flow and wet the fiber, providing more surface area for exposure to air. The hydroxyl groups and acid groups could also cross-link upon curing to provide durability to the substrate. That is, in some examples, the polymer may dry as a hard coating.

A visible light activated antimicrobial coating composition is obtained by the monomers described herein. The coating described herein can be used under indoor lighting conditions. The antimicrobial coating composition exhibits antimicrobial activity under visible light and in reduced light.

An exemplary emulsion polymer was designed for durability and water resistance, but also removability. Removability was achieved by incorporation of a large number of carboxylic acid groups at low pH (3-5), then use of an alkaline remover solution. Efficiency was achieved by means of core/shell architecture, in which the Rose Bengal monomer was incorporated only in the shell of the particle, keeping it on the surface and not embedded deep within the polymer film.

Generally, long chain polymer molecules are synthetized by two types of polymerization, step growth and chain growth. Step growth is based on chemical reactions such as esterification or amidation. Chain growth is an alternative way to get long chain polymers. Chain growth is based on the opening of unsaturated bonds on monomers by initiators. Compared with step growth, chain growth more easily generates high molecular weight polymers. Many functional polymers can be polymerized by chain copolymerization.

Polymerization of the monomers in the emulsion can be effected by a suitable initiation system, for example, UV initiator or thermal initiator.

Substrates treated with either type of polymer containing a dye, e.g., the Rose Bengal monomer or polymer containing the monomer become self-sanitizing upon exposure to light. This has been proven with fabric used for medical fabrics, kitchen wipes, filter media and sportswear. The emulsion polymer has been evaluated as a spray on floors, carpets, towels and garments as a means of reducing or eliminating odor from bacterial activity. It has also been evaluated in floor wax for providing self-sanitizing floor surfaces. It has also been proposed as a treatment for faucet handles and push plates in rest rooms and commonly touched surfaces such as stair railings and grocery cart handles.

Specific embodiments include a coating suitable to provide an antimicrobial surface that is one that presents an antimicrobial agent that inhibits or reduces the ability of microorganisms to grow. Antimicrobial agents are agents that kill microorganisms or inhibit their growth. Antimicrobial agents can be classified by the microorganisms that they act against. For example, antibacterials are used against bacteria, anti-fungals are used against fungi and anti-virals are used against viruses. Such surfaces are desirable to prevent the spread of infection and so are desirable in healthcare settings such as hospitals, hospices, retirement homes and clinics, for example. While a material may or may not be inherently antimicrobial, the present application is directed generally to surfaces which do not possess inherent or sufficient antimicrobial properties and require a surface treatment or coating to become antimicrobial.

Another embodiment includes a polymer obtained by selecting a first monomer; operatively linking the first monomer to a dye, e.g., Rose Bengal or operatively incorporating the Rose Bengal, selecting a second monomer, polymerizing the first monomer and the second monomer using free radical polymerization. More than 50 percent of the first monomer can be linked to the Rose Bengal. The polymer may have less than 2% by weight of the first Bengal monomer. The polymer may have less than 1% by weight of the Rose Bengal operatively connected to the first monomer.

Any conventional process for making emulsion polymers may be suitable for preparing specific embodiments. Generally, latex emulsion polymers can be prepared by mixing the acid monomers with the hydrophobic monomers and surfactant together to form a monomer mixture. For example, emulsification can occur readily with mixing hydrophobic monomers and surfactant in water. Typically, a monomer mixture can be prepared by charging water and dissolving surfactant in the water. Acid monomers and hydrophobic monomers can then be added. The homogenization can be optionally facilitated by the use of homogenizing equipment and/or non-copolymerizable surfactants (e.g. ethoxylates) compatible with the temporary composition. A surfactant or surfactants can then be added to the monomer mixture and stirred to form an emulsion. The monomers are mixed with water and the copolymerizable surfactants to form a pre-emulsion, and then the monomers can be "stirred" to mix.

Alternatively, monomers and copolymerizable surfactants can be mixed (e.g. without water to form a monomer mixture). Often anionic surfactants or aqueous solutions of surfactants will not dissolve in pure monomer. The monomer pre-emulsion can be prepared from water, surfactant, acid monomers and hydrophobic monomers by any conventional means that is suitable, depending on the requirements of the specific components.

The surfactant(s) may include a copolymerizable surfactant, a noncopolymerizable surfactant, or a combination of copolymerizable and noncopolymerizable surfactants. In one embodiment, noncopolymerizable surfactants can be used to form the latex particle. The many parameters of emulsion polymerization techniques can be adjusted by those skilled in the art to obtain particular results such as particle size or freeze-thaw resistance. The monomers can be added to the aqueous phase gradually or in one charge. Monomers can be added continuously or in staggered finite increments.

Other ingredients can be added, as long as they are not deleterious to the antimicrobial and/or antiviral activity of the dye. For example, the singlet oxygen should not be quenched.

One specific embodiment includes copolymerizable surfactants, due to performance benefits from them being incorporated into the polymer. For example, the inability to migrate to the surface can reduce re-wetting and water-sensitivity. In one specific embodiment, the temporary coating prepared using copolymerized surfactants produced significantly less foam during the removal process as compared to traditional coatings. The reduction in foam can minimize slip hazards and allow for improved flocculation in waste water disposal.

The temporary coating may include a balanced formulation of hard monomers, soft monomers and copolymerizable surfactants to achieve a desired glass transition temperature (Tg). In one example, the monomers were balanced to achieve a Tg of −10 degrees. C. Further, in other examples, the overall Tg of the polymer ranged from about 10 to 20 degrees C.

The polymers containing this Rose Bengal dye monomer have been applied to fabric of various types. Nonwoven nylon substrates are preferred. The polymer is applied at dry add-on levels of around 0.05%, giving the dried, cured fabric a pink color. Aging studies under continuous light show effective performance for at least 3 months. At 6 months performance may start to drop off. The dye photodegrades eventually and the pink color fades to a light beige. At this point there is less antimicrobial activity. There is also no anti-microbial activity on the pink fabric in the dark. Fabric permanently bonded with the solution polymer has been subjected to over 25 simulated home launderings with less than 10 ppm leaching of the dye-containing polymer.

Other optional ingredients include, water, an amount of a suitable noncopolymerizable surfactant, thickeners, hiding pigments, opacifiers, colorants, antioxidants, biocides or any other ingredients typically added to latex polymers. Optional ingredients include conventional dispersants. These additional ingredients are not critical to the function of the coating but may aid in improving the commercial utility.

The core-shell polymer is designed to be removable under alkaline conditions such as laundering. It has been formulated as a dilute spray solution that can be sprayed on towels or athletic wear. Towels have been evaluated by pet groomers and found not to develop "doggy odor" over the course of a week. This reduced the amount of laundry required and reduced the amount of water used for this purpose. The spray had been sprayed on horse blankets and found to reduce the odor from a sweaty horse. No irritation or other ill effects were seen on the horse or rider. After a couple weeks of riding the blanket had become dirty, but not odiferous, and then required washing. It likewise has been found that spraying athletic wear with this allows clothing to be worn for workouts all week without building an objectionable odor. Untreated garments required washing after each use.

In one embodiment, the polymer is placed on non-woven fabrics such as washing and wiping cloths, diapers, sanitary napkin covers, hospital gowns, surgical drapes, sheets, pillow cases, curtains, backing material for garments, table cloths, bed spreads, sponges, underpads, etc. For these products and products such as sheets, pillow cases, hospital gowns and surgical drapes in particular, it is highly desirable to render the non-woven textiles or other non-woven type materials antimicrobial and/or antiviral. Indeed, the passage of liquid through surgical drapes, which are used during surgical procedures to isolate the patient from the operating room personnel and environment, is one source of bacterial contamination.

Certain embodiments have advantages in that the polymers are safer in both application and administration. For example, a polymer may be large enough to hinder absorption by cells. Further, a polymeric form may be safer to handle over a dust form. When the polymer containing the Rose Bengal is bonded to fabric or a substrate, there can be less migration of the Rose Bengal from the substrate and less leach out either in use or after disposal.

In another embodiment, the polymer or coating may be applied to animals, animal quarters, animal-traveled areas, and ill animals to treat and prevent microbial and viral agents/infections.

There are several advantages of singlet oxygen antimicrobial technology cited. No heavy metals like silver, copper or mercury are involved. No or less toxic or poisonous chemicals are involved in dilute form such as the preservatives used in many industrial and consumer products. The treated substrates are inert and harmless to humans. A disadvantage of photo-catalytically generating singlet oxygen is that it requires light. It does not work in the dark. Other advantage of certain polymers is the polymers may be manufactured safer and more efficiently and use effectly $10^{th}$ to $100^{th}$ the amount of dye to produce optimal activity.

In certain embodiment, the second monomer can be an acrylic acid, methyl methacrylate (MMA), Methacrylic acid, Ethyl methacrylate (EMA), and/or n-Butyl methacrylate (BMA). Suitable Acrylates include Acrylic acid, 4-Acryloylmorpholine, [2-(Acryloyloxy)ethyl]trimethylammonium chloride, 2-(4-Benzoyl-3-hydroxyphenoxy)ethyl acrylate, Benzyl 2-propylacrylate, 2-Butoxyethyl acrylate, Butyl acrylate, tert-Butyl acrylate, 2-[(Butylamino)carbonyl]oxy] ethyl acrylate, tert-Butyl 2-bromoacrylate, 4-tert-Butylcyclohexyl acrylate, 2-Carboxyethyl acrylate, 2-Carboxyethyl acrylate oligomers anhydrous, 2-(Diethylamino)ethyl acrylate, Di(ethylene glycol)ethyl ether acrylate technical grade, Di(ethylene glycol) 2-ethylhexyl ether acrylate, 2-(Dimethylamino)ethyl acrylate, 3-(Dimethylamino)propyl acrylate, Dipentaerythritol penta-/hexa-acrylate, 2-Ethoxyethyl acrylate, Ethyl acrylate, 2-Ethylacryloyl chloride, Ethyl 2-(bromomethyl)acrylate, Ethyl cis-(β-cyano)acrylate, Ethylene glycol dicyclopentenyl ether acrylate, Ethylene glycol methyl ether acrylate, Ethylene glycol phenyl ether acrylate, Ethyl 2-ethylacrylate, 2-Ethylhexyl acrylate, Ethyl 2-propylacrylate, Ethyl 2-(trimethyl silylmethyl)acrylate, Hexyl acrylate, 4-Hydroxybutyl acrylate, 2-Hydroxyethyl acrylate, 2-Hydroxy-3-phenoxypropyl acrylate, Hydroxypropyl acrylate, Isobornyl acrylate, Isobutyl acrylate, Isodecyl acrylate, Isooctyl acrylate, Lauryl acrylate, Methyl 2-acetamidoacrylate, Methyl acrylate, Methyl α.-bromoacrylate, Methyl 2-(bromomethyl)acrylate, Methyl 3-hydroxy-2-methylenebutyrate, Octadecyl acrylate, Pentabromobenzyl acrylate, pentabromophenyl acrylate, Poly(ethylene glycol)methyl ether acrylate, Poly(propylene glycol) acrylate, Poly(propylene glycol)methyl ether acrylate Soybean oil, epoxidised acrylate, 3-Sulfopropyl acrylate potassium salt, Tetrahydrofurfuryl acrylate, 3-(Trimethoxysilyl)propyl acrylate, 3,5,5-

Trimethylhexyl acrylate. It was found that nitrogen-containing monomers such as acrylamide, acrylonitrile and N,N-dimethyl acrylamide could quench the singlet oxygen.

Preferably Methyl acrylate, acrylic acid, Ethyl acrylate (EMA), and/or n-Butyl acrylate (BMA) are used. Acrylamides: 2-Acrylamidoglycolic acid, 2-Acrylamido-2-methyl-1-propanesulfonic acid, 2-Acrylamido-2-methyl-1-propanesulfonic acid sodium salt solution, (3-Acrylamidopropyl)trimethylammonium chloride solution, 3-Acryloylamino-1-propanol solution purum, N-(Butoxymethyl)acrylamide, N-tert-Butylacrylamide, Diacetone acrylamide, N,N-Dimethylacrylamide, N-[3-(Dimethylamino)propyl]methacrylamide, N-Hydroxyethyl acrylamide, N-(Hydroxymethyl)acrylamide, N-(Isobutoxymethyl)acrylamide, N-Isopropylacrylamide, N-Isopropylmethacrylamide, Methacrylamide, N-Phenylacrylamide, N-[Tris(hydroxymethyl)methyl]acrylamide, In certain embodiments, the first monomer can be a styrene operatively connected to Rose Bengal. These include Styrene, Divinyl benzene, 4-Acetoxystyrene, 4-Benzyloxy-3-methoxystyrene, 2-Bromostyrene, 3-Bromostyrene, 4-Bromostyrene, .α.-Bromostyrene, 4-tert-Butoxystyrene, 4-tert-Butylstyrene, 4-Chloro-.α.-methylstyrene, 2-Chlorostyrene, 3-Chlorostyrene, 4-Chlorostyrene, 2,6-Dichlorostyrene, 2,6-Difluorostyrene, 1,3-Diisopropenylbenzene, 3,4-Dimethoxystyrene, α.,2-Dimethyl styrene, 2,4-Dimethyl styrene, 2,5-Dimethylstyrene,N,N-Dimethylvinylbenzylamine, 2,4-Diphenyl-4-methyl-1-pentene, 4-Ethoxystyrene, 2-Fluorostyrene, 3-Fluorostyrene, 4-Fluorostyrene, 2-Isopropenylaniline, 3-lsopropenyl-α.,α.-dimethylbenzyl isocyanate, Methylstyrene, .α.-Methylstyrene, 3-Methylstyrene, 4-Methylstyrene, 3-Nitrostyrene, 2,3,4,5,6-Pentafluorostyrene, 2-(Trifluoromethyl)styrene, 3-(Trifluoromethyl)styrene, 4-(Trifluoromethyl)styrene, 2,4,6-Trimethyl styrene. Preferably Styrene is used.

In certain embodiments, the polymers can be vinyl Groups. For example, 3-Vinylaniline, 4-Vinylaniline, 4-Vinylpyridine, 4-Vinylanisole, 9-Vinylanthracene, 3-Vinylbenzoic acid, 4-Vinylbenzoic acid, Vinylbenzyl chloride, 4-Vinylbenzyl chloride, (Vinylbenzyl)trimethylammonium chloride, 4-Vinylbiphenyl, 2-Vinylnaphthalene, 2-Vinylpyridine, N-Vinyl-2-pyrrolidinone, 2-Vinylnaphthalene, Vinyl acetate, Vinyl benzoate, Vinyl 4-tert-butylbenzoate, Vinyl chloroformate, Vinyl chloroformate, Vinyl cinnamate, vinyl decanoate, vinyl neodecanoate, vinyl neononanoate, vinyl pivalate, vinyl propionate, vinyl stearate, and vinyl trifluoroacetate.

Other monomers which may be used are those which have groups to help stabilisation of the particles, e.g. Poly(ethylene glycol)methyl ether acrylate, Poly(ethylene glycol)phenyl ether acrylate, lauryl methacrylate, Poly(ethylene glycol)methyl ether acrylate, Poly(propylene glycol)methyl ether acrylate, Lauryl acrylate and fluorinated monomers of above.

Other embodiment may include the use of anionic dyes and cationic dyes that are capable of generating singlet oxygen. Anionic dyes that provide a source of singlet oxygen include fluorescein derivatives (e.g.), preferably the alkali metal salts of Rose Bengal, 4,5,6,7-tetrachloro-2',5',7'-tetraiodo fluorescein sodium or potassium—(hereinafter, reference to Rose Bengal means an alkali metal salt thereof). Cationic dyes may include 3-amino-7-(dimethylamino)-2-methylphenothiazin-5-ium chloride (also known as Tolonium chloride or Toluidine Blue O), Thionin and Methylene Blue. Another dye may be tetraphenylporphyrin. The monomer is created by operatively linking the dyes by the respective carboxylic acid/salt group. The dyes may be used alone or in combination.

Other optional ingredients include, water, an amount of a suitable noncopolymerizable surfactant, thickeners, hiding pigments, opacifiers, colorants, antioxidants, biocides or any other ingredients typically added to latex polymers. Optional ingredients include conventional dispersants. These additional ingredients are not critical to the function of the coating but may aid in improving the commercial utility.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

An exemplary formulation: A Ter-polymer of methacrylic acid (17.5%), methyl methacrylate (7.5%), butyl acrylate (50%) and veova-10 (25%).

| Deionized Water: | 200 g |
|---|---|

Initial Cat:

| | |
|---|---|
| DI water | 1.5 |
| Ammonium Persulfate(APS) | 0.15 |
| DI Water | 40 |
| Ammonium Persulfate | 1.0 |
| t-Butyl Hydro peroxide | 0.3 |
| E-sperse 100 | 0.2 |

Monomer Mix:

| | |
|---|---|
| DI Water | 200.0 |
| Methacrylic Acid | 70.0 |
| Sodium Bicarbonate | 0.5 |
| KH-10 | 3.0 |
| Sodium dodecyl sulfate, 25% | 8.0 |
| E-sperse 100, 60% | 6.0 |
| Veova-10 | 100.0 |
| Butyl Acrylate | 200.0 |
| Methyl Methacrylate | 30.0 |
| Rose Bengal Derivative | 0.06 |
| Rinse water | 5.0 |

Rinse:

| | |
|---|---|
| DI Water Chase: | 5.0 |
| tBHP | 0.3 |
| Ferrous sulfate 0.1% | 2.0 |
| APS | 0.1 |
| DI Water | 1.0 |
| SMBS | 0.1 |
| DI Water | 1.0 |
| APS | 0.1 |
| DI Water | 1.0 |
| SMBS | 0.1 |
| DI Water | 1.0 |

In this example, to prepare a core-shell polymer, the first monomer or monomer operatively connected to the Rose Bengal is withheld from the core monomer pre-emulsion, which may comprise 50 to 95% of the polymer. When the core has been added to the reaction, the shell monomer pre-emulsion is prepared and added.

Example 2—Sample Methodology

Dionized water was agitated in a kettle and heated to about 80'C. While the kettle was heating, the monomer pre-emulsion was formulated. Methacrylic acid and sodium bicarbonate were charged. KH-10 was dissolved and mixed thoroughly. Veova-10, butyl acrylate and methyl methacrylate were continually mixed.

Delayed catalyst was added to DI water in a catalyst tank and ammonium persulfate was added. E-sperse 100 and t-BHP was added. Prepared initial catalyst by charging DI water to catalyst pail was stirred in ammonium persulfate.

Upon reaching 80'C and stabilizing, $N_2$ and charge 3% initial monomer. Charge initial catalyst and hold 15 minutes. Monomer delay was 180 minutes and catalyst delay was about 200 minutes. The batch was maintained at 80-84'C for duration of the delays. When monomer was in, rinse water was added to tank and rinse was to reactor. After catalyst delay is in, hold for about 15 minutes. tBHP and ferrous sulfate solution was added and held for 15 minutes. Batch cooled to 60-65'C. Chase 2 times with tBHP/SMBS combination, waiting 15 minutes between chases. Residual free monomer was examined. When in specification, cool to 50'C or less. Sample for final adjustments.

pH: 3.0-5.0 Viscosity (RV, #3, 100 rpm): <300 cps
Free monomers: <200 ppm solids: 44-46% (tentative)
Ingredients in Formulation
Deionized water, Ammonium persulfate (APS), t-butyl hydro peroxide (tBHP), sodium bicarbonate, sodium dodecyl sulfate, methacrylic acid, methyl methacrylate, butyl acrylate
Veova 10 (neodecanoic acid ethenyl ester), Ferrous sulfate Sodium meta bisulfite (SMBS), E-sperse 100, KH-10 (blend: Poly(oxy-1,2-ethanediyl), -sulfo-[[1-[2-propenyloxy)methyl]undecyl]oxy]-,ammonium salt (R=C10) and Poly(oxy-1,2-ethanediyl), -sulfo-[[1-[2-propenyloxy)methyl]tridecyl]oxy]-,ammonium salt (R=C12))*CV5666 (Benzoic Acid, 2,3,4,5-tetrachloro-6-(6-hydroxy-2,4,5,7-tetraiodo-3-oxo-3H-xanthen-9-yl)-ethenylphenyl)methyl ester) E-sperse 100: distyryl phenol ethoxylate, sulfate, ammonium salt, from Ethox Chemical Co, Greenville, S.C.
In this example, to prepare a core-shell polymer, the first monomer or monomer operatively connected to the Rose Bengal is withheld from the core monomer pre-emulsion, which may comprise 50 to 95% of the polymer. When the core has been added to the reaction, the shell monomer pre-emulsion is prepared and added.

Example 3. Solution Polymer

Kettle Charge:

| | |
|---|---|
| DI H2O | 465.0 |
| FeSO4, 0.1% in H2O | 2.2 |
| KH-10 | 0.5 |
| Propylene glycol | 29.9 |

Monomer Mix:

| | |
|---|---|
| Propylene glycol | 47.4 |
| Itaconic Acid | 8.2 |
| CV 5666 | 4.36 |
| Hydroxy ethyl methacrylate | 3.48 |
| Allyl alcohol/10EO | 3.48 |
| KH-10 | 2.38 |
| Acrylic acid | 140.8 |

Initial Oxidant:

| | |
|---|---|
| DI H2O | 2.0 |
| Ammonium persulfate(APS) | 0.2 |

Initial Reductant:

| | |
|---|---|
| DI H2O | 2.0 |
| Sodium meta bisulfite (SMBS) | 0.2 |

Delay Oxidant:

| | |
|---|---|
| DI H2O | 40.9 |
| APS | 0.44 |

Delay Reductant:

| | |
|---|---|
| DI H2O | 40.9 |
| SMBS | 0.44 |

Monomer Rinse:

| | |
|---|---|
| Acrylic acid | 1.9 |
| HEMA | 0.4 |
| Acrylic acid | 1.9 |
| HEMA | 0.4 |

Rinse Water:

| | |
|---|---|
| DI H2O | 5.0 |
| DI H2O | 5.0 |

Chase:

| | |
|---|---|
| DI H2O | 2.0 |
| APS | 0.2 |
| DI H2O | 2.0 |
| Sodium formaldehyde sulfoxylate | 0.2 |
| DI H2O | 2.0 |
| APS | 0.2 |
| DI H2O | 2.0 |
| SFS | 0.2 |
| 586 biocide | 0.1 |

Example 4

This example confirms the antimicrobial effects of Rose Bengal when bound to a substrate. A face mask, covering the mouth and nose, comprising at least 1 thin layer of treated fabric, so that it may provide a means of singlet oxygen inhalation therapy to one wearing it facing a light source for treatment of bacterial and viral respiratory infections. Specifically, the material was place on a person's nose and mouth for 3 minutes. The cold passed in 2 days. Multiple treatments may be needed.

Example 5

A nonwoven material was saturated as a continuous web on a pilot line saturator with the formulas.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

What is claimed:

1. A structure for delivering singlet oxygen in the presence of light comprising:
    a substrate;
    a polymer disposed on the substrate comprising an acid functional monomer, a co-polymerizable derivative of Rose Bengal, the Rose Bengal copolymerized with the acid functional monomer, a co-polymerizable surfactant copolymerized with the Rose Bengal, the Rose Bengal is in a core shell architecture, and the core comprises a hydrophobic polymer and the Rose Bengal is contained in the shell, and wherein the surfactant is selected from the group consisting of ionic surfactants, anionic surfactants, cationic surfactants, nonionic surfactants, zwitterionic surfactants, and mixtures thereof; the polymer having Rose Bengal in polymer in an amount to render the polymer antimicrobial or antiviral upon exposure of the substrate to light; and the polymer producing singlet oxygen by the Rose Bengal upon passage of air through the substrate in the presence of light.

2. The polymer of claim 1, wherein the co-polymerizable derivative of Rose Bengal has the following structure:

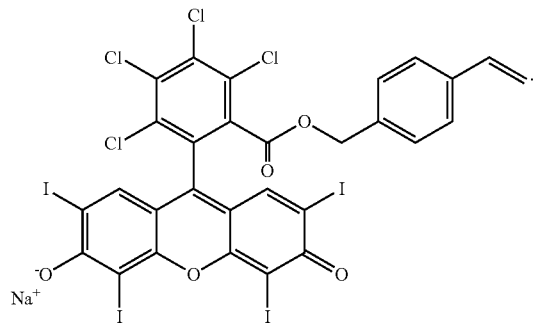

3. The polymer of claim 1, wherein the Rose Bengal is a dye.

4. The polymer of claim 1, wherein the operative connection between the Rose Bengal and the first monomer is a covalent bond.

5. The polymer of claim 1, wherein the acid functional monomer is one of an acrylic acid monomer, a methacrylic acid and itaconic acid.

6. The polymer of claim 1, wherein the surfactant and the acid functional monomer are polymerized through free radical polymerization.

7. The polymer of claim 1, wherein the polymer is a coating, the coating being between approximately 10 nm to 400 nm thickness.

8. The polymer of claim 1, wherein the surfactant is an hydroxy functional monomer.

9. The structure of claim 1, wherein the substrate forms a mask.

* * * * *